United States Patent [19]

Allan et al.

[11] Patent Number: 5,530,107

[45] Date of Patent: Jun. 25, 1996

[54] METHOD FOR MAKING STEROIDAL PERACYL GLYCOSIDES

[75] Inventors: Douglas J. M. Allan, New London; Frank R. Busch, Gales Ferry; John F. Lambert, North Stonington; Russell J. Shine, Waterford; Stanley W. Walinsky, Mystic, all of Conn.

[73] Assignee: Pfizer Inc., New York, N.Y.

[21] Appl. No.: 244,403

[22] PCT Filed: Oct. 15, 1992

[86] PCT No.: PCT/US92/08638

§ 371 Date: May 23, 1994

§ 102(e) Date: May 23, 1994

[87] PCT Pub. No.: WO93/11150

PCT Pub. Date: Jun. 10, 1994

[51] Int. Cl.$^6$ .............................. C07J 53/00; C07H 1/00
[52] U.S. Cl. .............................................. 536/6.1; 536/4.1
[58] Field of Search ................................ 536/4.1, 18.5, 536/6.1; 514/824

[56] References Cited

U.S. PATENT DOCUMENTS

| | | | |
|---|---|---|---|
| 2,991,282 | 4/1961 | Rubin | 540/18 |
| 3,303,187 | 2/1967 | Rubin | 540/18 |
| 3,935,194 | 1/1976 | Loken | 260/239.55 |
| 4,260,603 | 4/1981 | Pegel et al. | 514/26 |
| 4,602,003 | 7/1986 | Malinow | 514/26 |
| 4,602,005 | 7/1986 | Malinow | 260/239.55 H |
| 5,010,185 | 4/1991 | Urban | 536/6.1 |

FOREIGN PATENT DOCUMENTS 0159431  10/1985  European Pat. Off. .......... C07J 71/00

OTHER PUBLICATIONS

Urban et al., Synthesis of Tigogenyl β–O–Cellobioside Heptaacetate and Glycoside Tetraacetate via Schmidt's Trichloroacetimidate Method; Some New Observations, Tetrahedron Letters, vol. 31, No. 31, pp. 4421–4424, 1990.

Agnew. Chem., vol. 86, No. 5, 1974, Gunter Wulff et al.: "Ergebnisse und Probleme der O–Glykosidsynthese", pp. 173–208.

Caglioti et al., Tetrahedron 19,1127 (1963)—discloses β–togogenin and its preparation.

K. Freudenberg and W. Nagari, Ann., 494,63 (1932)—discloses the synthesis of cellulose derivatives.

T. Kawasaki et al., Chem. Pahrm. Bull., Japan 10,698 (1962)—duscoses β–diosgenin and its preparation.

Malinow et al., Steroids, vol. 48, pp. 197–211, 1986—discloses the synthesis of togogenin beta–O–cellobioside.

Marker et al., J. Amer. Chem. Soc., 69, 2167–2211 (1947)—discloses β–hecogenin and its preparation.

Schmidt, Angew. Chem. Int. Ed. Engl., vol. 25, pp. 212–235 (1986)—discloses the synthesis and reactions of O–glycosyl trichloroacetimidates.

Primary Examiner—John W. Rollins
Attorney, Agent, or Firm—Peter C. Richardson; Gregg C. Benson; A. Dean Olson

[57] ABSTRACT

Processes for the synthesis of tigogenin beta-O-cellobioside heptaalkanoate which is an intermediate for the known hypocholesterolemic agent tigogenin beta-cellobioside. The process comprises reacting α-cellobiosyl bromide heptaalkanoate and β-tigogenin in the presence of zinc fluoride or zinc cyanide under conditions capable of forming said tigogenyl β-O-cellobioside heptaalkanoate. The analogous preparations of hecogenin β-O-cellobioside heptaalkanoate, 11-ketotigogenin β-O-cellobioside heptaalkanoate, and diosgenin β-O-cellobioside heptaalkanoate are also disclosed. The process provides both high β-anomeric selectivity and high yields.

12 Claims, No Drawings

METHOD FOR MAKING STEROIDAL PERACYL GLYCOSIDES

This application was filed under 35 U.S.C. §371 based on PCT/US92/08638, which was filed on Oct. 15, 1992 which is a continuation of U.S. application Ser. No. 07/797,574 which was filed on Nov. 25, 1991 and is now abandoned.

BACKGROUND OF THE INVENTION

The present invention relates to processes for the synthesis of steroidal glycosides, and particularly to the preparation of steroidal peracyl glycosides used as intermediates therein.

Tigogenin beta-O-cellobioside is a known compound having utility in the treatment of hypercholesterolemia and atherosclerosis (Malinow, U.S. Pat. Nos. 4,602,003 and 4,602,005; Malinow et al., Steroids, vol. 48, pp. 197–211, 1986). Each patent disc;loses a different synthesis of this compound from alpha-D-cellobiose octaacetate; the first via the glycosyl bromide heptaacetate which is coupled with tigogenin in the presence of silver carbonate, and finally hydrolyzed; and the second via direct stannic chloride catalyzed coupling of the cellobiose octaacetate with tigogenin in methylene chloride, again followed by hydrolysis. In Malinow et al., reaction of cellobiose octaacetate with titanium tetrabromide gave the cellobiosyl bromide heptaacetate, which was coupled with tigogenin by means of mercuric cyanide, and then hydrolyzed. All of these methods have serious drawbacks for producing bulk material to be used as a pharmaceutical drug. A desirable goal, met by the present invention, has been to devise synthetic methods which avoid toxic and/or expensive reagents, and which cleanly produce the desired tigogenin beta-O-cellobioside, avoiding tedious and expensive purification steps.

Schmidt, Angew. Chem. Int. Ed. Engl., vol. 25, pp. 212–235 (1986) has reviewed the synthesis and reactions of O-glycosyl trichloroacetimidates formed by the reaction of sugars possessing a 1-hydroxy group (but with other hydroxy groups protected, e.g., by benzyl or acetyl) with trichloroacetonitrile in the presence of a base. There is preferential formation of the alpha-anomer when sodium hydride is used as base, and preferential formation of the beta-anomer when the base is potassium carbonate. The alpha anomer of tetrabenzylglucosyl trichloroacetimidate when coupled with cholesterol gave anomerio mixtures which varied with catalyst (p-toluenesulfonic acid or boron trifluoride etherate) and temperature(–40° to +20° C.). On the other hand, both the alpha and beta anomers of tetraacetylglucosyl analog reportedly yield exclusively beta-anomeric products.

Thus, there has been a continuing search in this field of art for improved methods of stereocontrolled syntheses of steroidal glycosides.

SUMMARY OF THE INVENTION

This invention is directed to a process for the synthesis of tigogenin β-O, 11-ketotigogenin β-O, hecogenin β-O, or diosgenin β-O cellobioside heptaalkanoate that provides greater β-anomeric selectivity and increased yields. The process is particularly useful for preparing tigogenin β-O-cellobioside heptaalkanoate, which is an intermediate for the known hypocholesterolemic agent tigogenin β-O-cellobioside. The process comprises reacting α-cellobiosyl bromide heptaalkanoate and β-tigogenin, 11-β-ketotigogenin, β-hecogenin or β-diosgenin in the presence of zinc fluoride or zinc cyanide under conditions suitable for forming the tigogenin β-O-, 11-ketotigogenin β-O, hecogenin β-O-, or diosgenin β-O-cellobioside heptaalkanoate.

Other features and advantages will be apparent from the specification and claims.

DETAILED DESCRIPTION OF THE INVENTION

Preferably the metal salt used in the stereospecific reaction of α-cellobiosyl bromide heptaalkanoate and β-tigogenin, 11-keto-β-tigogenin, β-hecogenin or β-diosgenin is zinc fluoride or zinc cyanide. It is especially preferred that the metal salt is zinc fluoride. It is preferred that about 0.5 equivalents to about 4 equivalents and especially preferred that about 1.5 equivalents to about 2.25 equivalents metal salt is used.

It may also be preferred to conduct the zinc fluoride or zinc cyanide-activated coupling in the presence of additional zinc salts such as zinc halides (e.g., zinc bromide, zinc chloride, zinc iodide) or basic salts of zinc (zinc oxide, zinc hydroxide, zinc hydroxy fluoride, zinc carbonate, etc.) to buffer or to activate the promoter (i.e., zinc fluoride or zinc cyanide metal salt). Trialkyl tertiary amines (e.g., diisopropylethyl amine, triethylamine, tributylamine), tetraalkylureas (e.g., tetramethyl urea, tetraethyl urea) or dialkylanilines (e.g., diisopropyl aniline, dibutylaniline) are also useful reaction buffers. The above additives are generally used at 10–50%. mole equivalents of the promoters.

Although any of the alkanoate ($C_1$–$C_4$) substituted alpha-cellobiosyl bromides may be used it is preferred that acetate (i.e., $C_1$) is used. They may be prepared from conventional starting materials according to methods described in K. Freudenberg and W. Nagai, Ann., 494,63 (1932) (e.g. Example 3). It is preferred that about 0.5 equivalents to about 3 equivalents, and especially preferred that about 1 equivalent to about 2 equivalents alkanoate ($C_1$–$C_4$) substituted alpha-cellobiosyl bromides are used.

Any reaction Inert solvent may be used. As used above and elsewhere herein, the expression "reaction-inert solvent" refers to a solvent which does not react or decompose with starting materials, reagents, intermediates or products in a manner which adversely affects the yield of the desired product. In general, the solvent can comprise a single entity, or contain multiple components. Preferably the solvent is a non-protic reaction inert solvent and it is especially preferred that the solvent is acetonitrile because of the excellent stereoselectivity it provides. Other solvents include methylene chloride, ethyl acetate and nitromethane.

It is preferred that the reaction is acid catalyzed as this can increase the selectivity of the β-cellobioside product over the α-cellobioside anomeric product. Preferably mineral acids are used. Hydrobromic acid has been shown to be particularly effective in increasing the β-cellobioside product yield. Other preferred acids include hydrochloric, hydrofluoric and sulfuric acid. It is preferred that about 0.05 equivalents to about 2 equivalents, and especially preferred that about 0.1 equivalents to about 0.5 equivalents add catalyst is used.

β-Tigogenin's preparation is described by Rubin in U.S. Pat. Nos. 2,991,282 and 3,303,187, by B. Löken in U.S. Pat.

No. 3,935,194 and Caglioti et al., Tetrahedron 19, 1127 (1963). Its structure is depicted below.

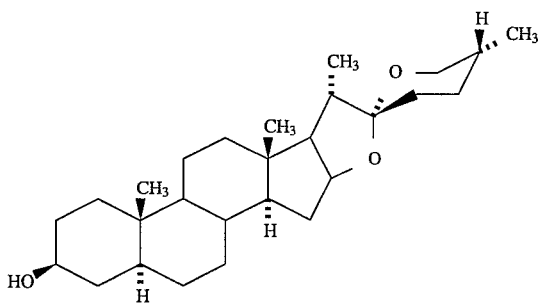

β-Hecogenin's preparation is described in a paper on Steroidal Sapogenins by Russell E. Marker et al., in J. Amer. Chem. Soc., 69, 2167–2211 (1947). Its structure is depicted below.

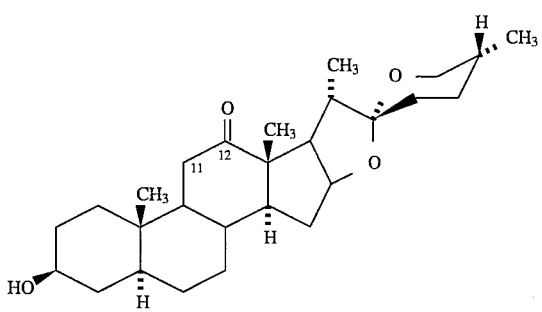

11-Keto-β-tigogenin switches the carbonyl group from the 12 position to the 11 position of the structure depicted above. 11-Keto-β-tigogenin is prepared from hecogenin by the following procedure. According to the procedure of Conforth, et al., (J. Chem. Soc., 1954, 907), hecogenin is acetylated, brominated, treated with sodium hydroxide and reduced with zinc to give the 12-hydroxy-11-keto analog. Then 12-hydroxy-11-keto analog is acetylated and reduced with calcium and ammonia to give 11-ketotigogenin.

β-Diosgenin's preparation is described in "Diosgenin and Other Steroidal Drug Precursors" by Asoikar, L. V., Chadha, Y. R., and Rawat, P. S., Council of Scientific and Industrial Research, New Delhi, India, 183 pages, 1979 and also in T. Kawasaki et al., Chem., Pharm. Bull., Japan 10 698 (1962). Its structure is depicted below.

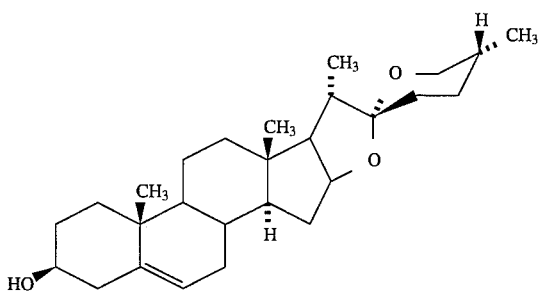

Preferably about 1 equivalent to about 2 equivalents of the steroid is used. It is especially preferred that about 1 equivalent to about 1.5 equivalents of the steroid is used.

Any environment or conditions (e.g., temperature, time, solvent) suitable for (i.e., capable of) forming the desired tigogenin, 11-ketotigogenin, hecogenin- or diosgenin-beta-O-cellobioside heptaalkanoate may be used. However, it is preferred that the reaction occurs at a temperature of about 20° C. to about 100° C. and preferably from about 50° C. to about 65° C. Below about 20° C. the reaction can be slow and above about 100° C. undesired side reactions (e.g. anomerization) can occur. This reaction is conveniently carried out at ambient pressure however, pressures from about 0.5 to about 3 atmospheres may be used.

Preferably the steroid, metal salt and solvent are heated to reflux and sufficient solvent is azeotropically distilled to remove substantially all the water. Then the cellobiosyl bromide heptaacetate is added to the above mixture and heated for about 0.5 to about 6.0 hours, typically under nitrogen. The desired compounds are then isolated by conventional methods.

For example, the glycosides may be precipitated from the crude filtered reaction mixture (e.g. acetonitrile product solution) by the addition of about 25% to 75% water and the remainder alcohol (e.g. methanol). Precipitation of the product from aqueous methanol/acetonitrile requires less processing than an extractive isolation, and provides a product of greater purity.

The steroidal peracyl glycosides may be deacetylated by conventional methods such as treatment with triethylamine in methanol, basic anion exchange resins or sodium methoxide in methanol or methanol/THF solvents (e.g. Example 2 below). For example, the deacetylated product may be prepared by refluxing in methanol/THF using a non-catalytic amount of sodium methoxide followed by conventional work-up. The excess methoxide is used to decompose the fluoro sugar, if any β-cellobiosyl fluoride heptaacetate is present, otherwise the deacetylation would be catalytic in sodium methoxide. The tigogenyl-β-O-cellobioside or analogs are then isolated by conventional methods such as filtration.

Although the above process is designed to synthesize steroidal glycosides of the β configuration, the more thermodynamically stable α-anomers are accessible by acid-catalyzed isomerization of the β-glycosides. For example, tigogenyl α-O-cellobioside heptaalkanoate can be prepared from tigogenyl β-O-cellobioside heptaalkanoate by heating the β-glycoside in a methylene chloride solution containing hydrogen bromide.

The influence of reaction stoichiometry, temperature, solvents, molecular sieves, and vestigial hydrogen bromide on the stereoselectivity and yield of tigogenyl β-O-cellobioside heptaacetate (using the process of Example 1) are summarized in Table 1.

TABLE 1

Zinc Fluoride or Cyanide Activated Glycosidic Couplings with Tigogenin

| Equivalents | | | | | | β-Glycoside |
|---|---|---|---|---|---|---|
| Glycosyl-Br | Activator | Tigogenin | Solvent | Sieves | Time/Temp. | Yield |
| 2.00 | ZnF$_2$(4.00) | 1.0 | CH$_3$CN | No | 2.5 hrs/65° C. | 79% |
| 1.50 | ZnF$_2$(3.00) | 1.0 | CH$_3$CN | No | 2.5 hrs/65° C. | 68% |
| 0.50 | ZnF$_2$(1.00) | 1.0 | CH$_3$CN | No | 3.0 hrs/65° C. | 32% |
| 0.50 | ZnF$_2$(1.00) Hbr(0.38) | 1.0 | CH$_3$CN | No | 1.5 hrs/65° C. | 30% |
| 2.00 | ZnF$_2$(4.00) | 1.0 | CH$_2$Cl$_2$ | No | 3.0 hrs/43° C. | 10% |
| 2.00 | ZnF$_2$(4.00) | 1.0 | Toluene | 4Å | 20 hrs/65° C. | 25% (α-anomer) 41% |
| 2.00 | ZnF$_2$(4.00) | 1.0 | CH$_2$Cl$_2$/CH$_3$CN (²/₁₃) | No | 1.5 hrs/65° C. | 64% |
| 1.00 | ZnF$_2$(2.00) Hbr(0.75) | 2.0 | CH$_3$CN | No | 1.0 hrs/65° C. | 30% |
| 0.50 | ZnF$_2$(0.50) | 1.0 | CH$_3$CN | No | 22 hrs/50° C. | 38% |
| 2.00 | ZnF$_2$(4.00) | 1.0 | CH$_3$CN | No | 1.75 hrs/80° C. | 76% |
| 0.50 | ZnF$_2$(0.50) | 1.0 | CH$_3$CN | No | 1.75 hrs/80° C. | 53% |
| 1.25 | ZnF$_2$(2.25) | 1.0 | CH$_3$CN | No | 1.75 hrs/80° C. | 61% |
| 2.00 | Zn(CN)$_2$(4.00) | 1.0 | CH$_3$CN | No | 2.0 hrs/65° C. | 63% |
| 2.10 | Zn(CN)$_2$(5.60) | 1.0 | CH$_3$CN | No | 3.0 hrs/65° C. | 55% |
| 1.50 | Zn(CN)$_2$(4.00) | 1.0 | CH$_3$CN | No | 2.5 hrs/65° C. | 45% |

The zinc fluoride-activated glycoside coupling was repeated with hecogenin and diosgenin in analogous processes to the β-tigogenin glycosidic coupling of Example 1 below. The results with these other sterols are summarized in Table 2.

TABLE 2

Zinc Fluoride-Mediated Glycosidic Couplings with Hecogenin or Diosgenin

| Equivalents | | | | | | Yield |
|---|---|---|---|---|---|---|
| Glycosyl-Br | Activator | Sterol | Solvent | Sieves | Time/Temp. | β-Glycoside |
| 2.00 | 2.25 | Cholesterol (1.0) | CH$_3$CN | No | 2.25 hrs/65° C. | 63% |
| 2.00 | 2.25 | Hecogenin (1.0) | CH$_3$CN | No | 3.0 hrs/65° C. | 72% |
| 2.00 | 2.25 | Diosgenin (1.0) | CH$_3$CN | No | 2.5 hrs/65° C. | 65% |

This invention makes a significant advance in the field of steroidal glycosides by providing efficient methods of preparing steroidal peracyl glycosides. The deacetylated end products are useful as antihypercholesterolemic agents.

It should be understood that the invention is not limited to the particular embodiments shown and described herein, but that various changes and modifications may be made without departing from the spirit and scope of this novel concept as defined by the following claims.

EXAMPLE 1

Tigogenyl β-O-Cellobioside Heptaacetate

To a dry flask equipped with a mechanical stirrer, thermometer, and distillation head were added β-tigogenin (4.16 g; 0.01 mole), anhydrous zinc fluoride (4.13 g; 0.04 mole), and 160 ml of dry acetonitrile. The slurry was heated to reflux (85° C.) and 90 ml of distillates was removed overhead while 60 ml of fresh, dry acetonitrile was added to the slurry. The mixture was cooled to 25° C. and then a sample was removed for a Karl Fisher determination (K.F.=0.02% H$_2$O). α-Cellobiosyl bromide heptaacetate (14.00 g; 0.02 mole) was added to the flask, and then the stirred slurry was heated to 65° C. under a nitrogen atmosphere. The mixture was maintained at 65° C. for 2.5 hours when thin-layer chromatography[1] (tlc) showed that the reaction was complete. The reaction was cooled to ambient temperature and 130 ml of methylene chloride was added. The thin slurry was filtered through Celite and the filtrate (300 ml) was washed with a saturated sodium bicarbonate solution (70 ml) followed by an aqueous wash (70 ml). After the organic layer was dried over anhydrous sodium sulfate (20 grams) and filtered; the solution was then concentrated to 50 ml via a distillation at atmospheric pressure. Two hundred milliliters of 2B-ethanol was added to the warm concentrate and the turbid solution was concentrated to approximately 50 ml. The thin slurry was cooled to 25° C. and then it was granulated for 90 minutes at room temperature. The crude product was filtered, the cake was washed with 25 ml of 2B-ethanol, and then dried at 40° C. in vacuo for 17 hours to give 10.8 grams of white crystalline solids (m.p.= 226°–231° C.).

[1] K. Freudenberg and W. Nagari, Ann., 494, 63 (1932).

The solids were dissolved in 25 ml of methylene chloride and then 75 ml of 2B-ethanol was added. The thin slurry was heated to reflux (760 mm) and 35 ml of distillate was removed overhead. The resulting slurry was cooled to room temperature and then was granulated for 90 minutes. The β-glycoside was filtered, and then dried at 40° C. in vacuo for 18 hours to give 9.65 grams of a while crystalline solid (m.p.=229°–234° C.), Thin-layer chromatography[1] and high pressure liquid chromatography[2] (hplc) show that the product contains 77% (w/w) tigogenyl β-O-cellobioside heptaacetate and 15% (w/w) α-cellobiosyl fluoride heptaacetate. The α-cellobiosyl fluoride heptaacetate is most easily removed from the product during the deacetylation step.

[1]K. Freudenberg and W. Nagari, Ann., 494, 63 (1932).
[2]Merck Pre-Coated TLC Silica Gel 60F-254 Plates using a toluene/acetic acid (4:1) eluant. Plates were sprayed with 10% (w/w) $H_2SO_4$ in water and heated for charring, after the plates were developed.

EXAMPLE 2

Tigogenyl β-O-cellobioside

Crude tigogenyl β-O-cellobioside heptaacetate (50.0 g; 0.048 moles) was dissolved in 250 ml of tetrahydrofuran and 250 ml of methanol while maintained under a nitrogen atmosphere. The hazy solution was filtered through a bed of Celite and then a solution of sodium methoxide (0.46 g; 0.008 moles) in methanol (10 ml) was added to the filtrate. The solution was heated to reflux (60° C.) and maintained at reflux for 1.25 hours generating a thick white slurry. A reaction aliquot was removed and analyzed by thin-layer chromatography which indicated that the reaction was complete. The slurry was concentrated by removing 200 ml of distillate and then 200 ml of water was added to the refluxing slurry. Another 200 ml of distillate was removed, and additional water (200 ml) was added. The slurry was cooled to ambient temperature and filtered. The product cake was washed with water (50 ml) and then pulled dry on the filter. The water-wet cake was heated to reflux (65° C. in 600 mls of THF and 92 mls of water). DARCO G-60 (1.53 grams) was added to the solution, stirred for 15 minutes, and then the mixture was filtered through Celite. The solution was concentrated by removing 460 ml of distillates and 460 ml of methanol was then added. The methanol addition and concentration sequence was repeated twice again removing an addition 800 mls of distillate and 800 mls of fresh methanol was added. The resulting slurry was cooled to 20° C. and then granulated for one hour. The product was filtered, rinse with fresh methanol (50 ml), and then the wet cake was reslurried in 300 mls of fresh methanol (24° C.). The product was filtered and then dried at 40° C. in vacuo overnight. Tigogenyl β-O-cellobioside (24.4 g; 0.036 moles) was isolated in 74% overall yield. Spectral and physical properties were identical to an authentic sample.

EXAMPLE 3

α-D-Cellobiosyl Bromide Heptaacetate

α-D-Cellobiosyl bromide heptaacetate was prepared form α-D-cellobiose octaacetate and hydrogen bromide in glacial acetic acid using a modified procedure of Freudenberg and Nagari[1].

[1]K. Freudenberg and W. Nagari, Ann., 494, 63 (1932).

A 20% (w/w) hydrogen bromide solution (1.78.7 g; 0.44 mole of HBr) in glacial acetic acid was prepared by bubbling gaseous hydrogen bromide into glacial acetic acid until a density of 1.212 was obtained. In a separate dry reactor maintained under a nitrogen atmosphere, α-D-cellobiose octaacetate (50.0 g; 0.074 moles) was dissolved in 408 ml of methylene chloride. The HBr/HOAC solution was added to the disaccharide solution to give a yellow solution. After the solution was stirred for 2 hours at −17°–25° C., a small aliquot of solution was removed for a reaction completion assay. Once thin-layer chromatography[2] indicated that the reaction was complete, the solution was cooled to 10° C. and 0.5 liters of water was added. The mixture was stirred for 10 minutes, the stirring was stopped, and the layers were allowed to separate. The methylene chloride layer was decanted and then washed with 7.5% w/w sodium bicarbonate solution (0.5 liters) followed by water (0.5 liters). Finally, the methylene chloride solution was dried over 8 grams of anhydrous magnesium sulfate and then filtered. The $MgSO_4$●hydrate cake was washed with fifty milliliters of fresh methylene chloride, and the filtrate and wash were combined. The methylene chloride solution was concentrated to approximately 0.15 liters by an atmospheric distillation and then cooled to ambient temperature. Diisopropyl ether (0.6 liters) was slowly added over 15 minutes with stirring to generate a thick slurry. The product was granulated for 1 hour at 25° C., filtered, and then dried in vacuo at 40° C. for 4.5 hours. α-Cellobiosyl bromide heptaacetate (47.6 g; 92% yield) was obtained as a white crystalline solid (m.p.= 192°–194° C.) whose $^1H$ NMR spectrum ($CDCl_3$) was consistent with its structure.

[2]Merck Pre-Coated TLC Silica Gel 60F-254 Plates using a toluene/acetic acid (4:1) eluant. Plates were sprayed with 10% (w/w) $H_2SO_4$ in water and heated for charring, after the plates were developed.

EXAMPLE 4

11-Ketotigogenyl-β-O-Cellobioside Heptaacetate

To an appropriately equipped one liter, 3-necked round bottom flask were added acetonitrile (305 mls), 11-ketotigogenin (5.00 g; 0.011 moles), and rhombohedral, crystalline zinc fluoride (1.65 g; 0.016 moles). The slurry was heated to reflux (80° C.) and then 100 ml of distillate was removed overhead. The slurry was cooled to room temperature, and then 15.39 grams (0.022 moles) of α-cellobiosyl bromide heptaacetate was added. The reaction mixture was reheated to 60°–65° C. and then maintained at 60°–65° C. for 2 hours. A reaction sample was removed for a reaction completion assay. Thin-layer chromatography assay (EtOAc/hexanes 1.5:1) showed the complete disappearance of the glycosyl bromide starting material so the reaction was cooled to 25° C. and 152 ml of methylene chloride was added. After stirring for 10 minutes, the mixture was filtered through Celite and the filter cake was washed with 25 ml of $CH_2Cl_2$. The combined reaction filtrate and wash were washed with water (81 mls), saturated sodium bicarbonate solution (76 mls), and water (137 ml). The organic layer was finally dried over 11 grams of anhydrous magnesium sulfate. The $MgSO_4$ was filtered and washed with 16 mls of fresh $CH_2Cl_2$. The filtrate and wash were combined and then concentrated at reduced pressure to one fourth its original volume (300 mls). 2B-Ethanol (250 ml) was added and the resulting solution was concentrated to one-half volume (170 mls). The slurry was cooled to 20°–25° C. and then granulated for 1 hour. The white waxy solids were filtered, washed with fresh 2B-ethanol (50 mls), and then dried in vacuo at 40° C. overnight. 11-ketotigogenyl-β-O-cellobioside heptaacetate (9.7 grams; m.p.=205°–219° C.) was isolated in 84% overall yield. Chromatographic and spectral characterization were identical to an authentic sample of 11-ketotigogenyl-β-O-cellobioside heptaacetate. Crude 11-ketotigogenyl-β-O-cellobioside could also be isolated in 64% yield by the following aqueous isolation sequence: The crude reaction mixture was diluted with additional fresh acetonitrile (50 ml) and then filtered through Celite. Methanol (290 mls) was added to the filtrate and the resulting solution was heated at reflux (65° C.) for one hour. One hundred milliliters of deionized water was slowly added to the refluxing solution to give a hazy mixture. After 20 minutes at reflux (72° C.), the mixture was slowly cooled to more temperature and then granulated at 23°–25° C. for 1 hour. The crude product was filtered and washed with water. The filter cake was suspended in 2B-ethanol (75 ml) and the mixture was heated to reflux. The mixture was then cooled to ambient temperature, filtered, and the solids were dried in vacuo at 40° C. overnight. 11-Ketotigogenyl-β-O-cellobioside heptaacetate was isolated in 64% overall yield.

EXAMPLE 5

11-Ketotigogenyl-β-O-Cellobioside

11-Ketotigogenyl-β-O-cellobioside heptaacetate (9.7 g; 9.2 mmoles) was suspended in 50 mls of methanol and 50 mls of tetrahydrofuran. The system was purged with nitrogen and then a solution of sodium methoxide (0.10 g; 1.9 mmoles) in methanol (1 ml) was added. The solution was heated to reflux (61° C.) and then maintained at reflux for 1 hour. Thin-layer chromatography ($CH_2Cl_2$/methanol 4:1) of the resulting slurry showed that the reaction was complete. The tetrahydrofuran was removed from the reaction by an atmospheric distillation and eventually displacement with methanol (220 mls). A total of 180 ml of distillate was collected. The slurry was cooled to 20°–25° C. and then granulated overnight. The product was filtered, washed with methanol (2×20 mls) and then the wet cake was reslurried (20 hours) in 100 ml of deionized water. After filtration and drying in vacuo at 25° C. overnight, 4.7 grams of 11-ketotigogenyl-β-O-cellobioside was isolated in 65.5% overall yield. The product was homogenous by tlc and analytical characterizations was consistent with the product's structure.

EXAMPLE 6

In Situ Hydrobromic Acid Generation

α-Cellobiosyl bromide heptaacetate (5.00 g; 7.15 mmole) and 50 ml of acetonitrile were added to a 75 ml round bottom flask which was equipped with a mechanical stirrer, thermometer, and vacuum distillation head. The system was purged with nitrogen and then the pressure was reduced to approximately 425 mm Hg. The solution was heated to 56°–58° C. and approximately 13 ml of distillate was removed overhead. The solution was cooled to room temperature and the vacuum was slowly released. Methylene chloride (37 ml) was added to the glycosyl bromide solution and then the solution was extracted with water (2×25 ml). The aqueous phases were combined and then titrated to a phenolphthalein endpoint using 0.1005 N NaOH solution.

The millequivalents of HBr acid contained in the α-cellobiosyl bromide heptaacetate solution before and after the azeotropic strip are reported below. The azeotropic strip increase the tetratable acid approximately 8–10 fold depending upon the water content.

| TITRATED ACIDS | |
|---|---|
| Initial α-Cellobiosyl Bromide Heptaacetate Solution | 2.1 milliequivalents |
| Azeotroped α-Cellobiosyl Bromide Heptaacetate Solution | 16.9 milliequivalents |

When the azeotropic distillation was used in Example 1 to dry the glycosyl bromide solution and to increase its acid content, the reaction time was decreased to 1.0 hour at 65° C. In addition, high yields and high β-anomeric selectivity were maintained.

EXAMPLE 7

Aqueous Isolation of Tigogenyl β-O-Cellobioside Heptaacetate

A zinc fluoride-mediated glycosidic coupling of β-tigogenin (0.915 mole) with α-cellobiosyl bromide heptaacetate (1.830 mole) in acetonitrile was conducted according to the procedure of Example 1. Once the reaction was complete, the crude reaction mixture was worked-up by an aqueous method to give high-quality tigogenyl β-O-cellobioside heptaacetate by the following sequence.

The crude reaction mixture was filtered through Celite to afford approximately 20 liters of a golden colored filtrate. The filtrate was heated (55°–60° C.) and concentrated at reduced pressure to about 10 liters. The concentrated solution was cooled to 50° C. and 5.0 liters of methanol was added. Subsequently, 7.5 liters of deionized water was slowly added over 30 minutes. A solid precipitated from solution once about 2 liters of water was charged. The mixture was heated to reflux (73° C.) and then maintained at reflux for 2 hours. The slurry was cooled to 25° C. and granulated overnight. The crude product was, filtered, washed with methanol (2×1.5 liters), and then dried in vacuo at 40° C. The crude solid (1.01 kg) was 95.5% pure by a hplc assay. In addition, the crude product contained only 1.3% of tigogenyl α-O-cellobioside heptaacetate and no β-cellobiosyl fluoride heptaacetate.

Crude tigogenyl β-O-cellobioside heptaacetate (1.0 kg) was slurried in 10.2 liters of 2B ethanol under nitrogen and then the mixture was heated to reflux (78° C.). After the slurry was at reflux for 1.5 hours, the mixture was cooled to 25° C. and then granulated for 12 hours. The product was filtered, washed with fresh ethanol (2×300 ml), and finally dried in vacuo at 40° C. overnight. Tigogenyl β-O-cellobioside heptaacetate (0.89 kg) was isolated in 74% overall yield from tigogenin. The white crystalline product was 98.9% pure by high pressure liquid chromatography and contained only 0.5% (w/w) of the isomeric α-anomer.

We claim:

1. A process for the synthesis of tigogenin-, 11-ketotigogenin-, hecogenin- or diosgenin-β-O-cellobioside heptaalkanoate comprising:

reacting α-cellobiosyl bromide heptaalkanoate

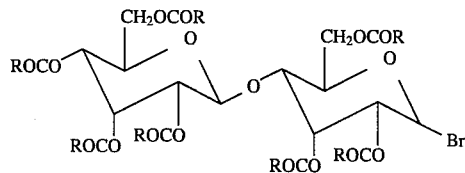

wherein R is $C_1$–$C_4$ alkyl and a steroid selected from the group consisting of β-tigogenin, 11-keto-β-tigogenin, β-hecogenin and β-diosgenin, in the presence of a metal salt selected from zinc fluoride and zinc cyanide under conditions capable of forming said tigogenin-, 11-ketotigogenin-, hecogenin- or diosgenin-β-O-cellobioside heptaalkanoate.

2. The process as recited in claim 1 wherein the metal salt is zinc fluoride, R is methyl and the reaction occurs in a non-protic reaction inert solvent.

3. The process as recited in claim 2 wherein the steroid is β-tigogenin or 11-keto-β-tigogenin.

4. The process as recited in claim 3 wherein said reaction occurs in the additional presence of an acid catalyst.

5. The process as recited in claim 4 wherein the acid catalyst is hydrobromic or hydrofluoric acid.

6. The process as recited in claim 5 wherein the reaction occurs in the additional presence of zinc bromide, zinc chloride, zinc iodide, zinc hydroxy fluoride, zinc oxide, zinc carbonate, zinc hydroxide, a trialkyl tertiary amine, a tetraalkyl urea or a N,N-dialkylaniline.

7. The process as recited in claim 6 wherein said reaction occurs at about 20° C. to about 100° C., about 1 to about 2 equivalents 11-keto-β-tigogenin is used, about 0.5 to about 4 equivalents zinc fluoride is used, and about 0.5 to about 3 equivalents α-cellobiosyl bromide heptaalkanoate is used.

8. The process as recited in claim 7 wherein the solvent is acetonitrile and about 0.05 to about 2 equivalents of hydrobromic acid is used.

9. The process as recited in claim 2 wherein the solvent is acetonitrile and additionally comprising the step of precipitating the 1-O-steroidal peracyl-β-glycosides from the acetonitrile by the addition of about 25% to about 75% water and the remainder alcohol.

10. The process as recited in claim 2 additionally comprising the step of deacetylating the tigogenyl β-O-Cellobioside heptaalkanoate to form tigogenyl β-O-cellobioside.

11. The process as recited in claim 10 wherein the deacetylation occurs by treatment with sodium methoxide in methanol.

12. The process as recited in claim 2 wherein the steroid is 11-ketotigogenin.

* * * * *